United States Patent
Moro et al.

(10) Patent No.: US 9,585,919 B2
(45) Date of Patent: Mar. 7, 2017

(54) PREPARATION FOR THE TREATMENT OF ITCHING AND INFLAMMATION ASSOCIATED WITH PSORIASIS AND OTHER TOPICAL SKIN MALADIES

(71) Applicants: Charles W Moro, Apopka, FL (US); Ron Moro, Apopka, FL (US)

(72) Inventors: Charles W Moro, Apopka, FL (US); Ron Moro, Apopka, FL (US)

(*) Notice: Subject to any disclaimer, the term of this patent is extended or adjusted under 35 U.S.C. 154(b) by 419 days.

(21) Appl. No.: 14/201,910

(22) Filed: Mar. 9, 2014

(65) Prior Publication Data
US 2015/0250830 A1 Sep. 10, 2015

(51) Int. Cl.
*A61K 35/62* (2006.01)

(52) U.S. Cl.
CPC .................... *A61K 35/62* (2013.01)

(58) Field of Classification Search
CPC ........................................ A61K 35/62
USPC ......................... 424/537, 543, 520
See application file for complete search history.

(56) References Cited

U.S. PATENT DOCUMENTS

| | | | | |
|---|---|---|---|---|
| 2002/0090669 A1* | 7/2002 | Hahn | ............ | A01N 63/02 435/41 |
| 2003/0017213 A1* | 1/2003 | Hahn | ............ | A01N 63/02 424/543 |
| 2013/0061521 A1* | 3/2013 | Cudmore | ............ | A01G 9/023 47/83 |
| 2013/0263786 A1* | 10/2013 | Meisel, III | ............ | C05F 17/0205 119/6.7 |

FOREIGN PATENT DOCUMENTS

| | | | |
|---|---|---|---|
| CN | 1682818 A | * | 10/2005 |
| CN | 103181443 A | * | 7/2013 |
| DE | 202010010603 U1 | * | 11/2010 |

OTHER PUBLICATIONS

Dr. Earth website document entitled "Earthworms: Anti-Aging Skin Care Miracle or Super Gross?" Jun. 30, 2011. 2-pages. Obtained from http://www.organicauthority.com/delicious-beauty/earthworms-anti-aging-skin-care-miracle.*
Strauss, A. New York Times article entitled "Fertilizer for the Face?" Jul. 4, 2012. 4-pages.*

* cited by examiner

*Primary Examiner* — Chris R Tate
(74) *Attorney, Agent, or Firm* — William R. Lovin; William Lovin & Assoc., LLC

(57) ABSTRACT

The present invention relates to a novel liquid preparation for the topical treatment for itching and inflammation associated with psoriasis and other common skin maladies wherein a layered mass of organic and inorganic material comprising: 1) Fruits, vegetable by-products, and paper scraps; 2) Grit comprising a blend of crushed volcanic rock; and, 3) A microbial soil enhancer is composted by a population of selected earthworms. The composting mass is misted daily to achieve a uniformly moist consistency. For the first two weeks, any worm tea (runoff) exiting the composting mass after each daily misting is recycled into the next day's misting fluid. A fraction of the worm tea produced during the third through twelfth weeks is harvested, pH adjusted, and treated with surfactant to form the liquid preparation.

1 Claim, No Drawings

PREPARATION FOR THE TREATMENT OF ITCHING AND INFLAMMATION ASSOCIATED WITH PSORIASIS AND OTHER TOPICAL SKIN MALADIES

CROSS-REFERENCE TO RELATED APPLICATIONS

This application claims benefit of U.S. Provisional Patent App. No. 61/775,650 filed Mar. 10, 2013 and incorporates it in its entirety by reference.

FIELD OF THE INVENTION

The present invention relates to a novel preparation for treating psoriasis and other topical skin maladies in general and in particular to a method of making a novel preparation for treating the itching and inflammation associated with psoriasis and other topical skin maladies by means of vermicultural techniques. The invention also discloses a method of topically applying the preparation.

BACKGROUND OF THE INVENTION

Psoriasis is a chronic, genetically predisposed disease of the skin that affects 2-3% of the world's population. There is no cure, but a number of treatments both topical and systemic are known to control many of the symptoms. The disease is chronic, although in many cases it tends to be a recurring disease with flares interspersed with periods of relative dormancy.

The most common form of psoriasis, plaque psoriasis, is commonly seen as red and white scaly patches appearing on the top first layer of the epidermis. Topical treatments range from moisturizers and mineral oil through topical corticosteroids through various vitamin $D_3$ analogs through retinol. Phototherapy has been used for years and generally comprises some form of ultraviolet (UV) treatment in conjunction with a topical treatment. Many systemic agents are used, the main ones of which are methotrexate, cyclosporine and various retinoids. More recently, various biologic agents have been developed. Biologic agents are proteins that affect the immune response that gives rise to psoriasis.

Alternative therapies have been suggested including changes in lifestyle and diet. Fasting, low energy diets, and vegetarianism have shown promise in some studies in the treatment of psoriasis while diets rich in fish oil are also thought to be helpful. One such alternative therapy known in the prior art deals with "worm tea"—the liquid containing dissolved worm castings recovered from earthworm beds. Organic farmers have for decades asserted that worm tea aids in the treatment of eczema and psoriasis. Indeed, products are commercially available that use worm tea as an active ingredient for the treatment of such disorders. Recently however, it has been discovered that worm tea produced in a composting environment rich in fruits, vegetables, raw paper, and volcanic grit that is admixed with a microbial soil enhancer and subsequently pH adjusted and treated with a plant surfactant exhibits heighted therapeutic effect. It is thus an object of the present invention to provide an improved worm tea derived topical preparation that demonstrates heightened efficacy when used to treat the itching and inflammation associated with psoriasis.

Moreover, given the similarities between the immune system response associated with psoriasis and many other inflammatory conditions of the skin, the improved worm tea of the present invention offers measurably significant levels of effectiveness when used to treat the itching and inflammation associated with a variety of skin maladies including, but not limited to, common skin rash, eczema, various fungal infections, rosacea, sunburn, insect bites, gangrenous pyoderma, keloids, and keratosis.

SUMMARY OF THE INVENTION

The present invention relates to a novel topical preparation that shows significant effectiveness treating the itching and inflammation associated with psoriasis and other topical skin maladies such as common skin rash, eczema, and acne and some effectiveness in the treatment of the itching and inflammation associated with various fungal infections, rosacea, sunburn, insect bites, gangrenous pyoderma, keloids, and keratosis.

The topical treatment is prepared by means of vermicultural techniques wherein a mass of organic garbage comprising fruits, vegetable by-products, and paper scraps is composted in a raised earthworm bed overseeded with a layer of grit comprising a blend of crushed volcanic rock and BioZome® microbial soil enhancer. This grit layer is, in turn, covered with a top layer of dairy cow manure. A mix of various earthworms is introduced into the beds. The beds are misted with natural spring water daily to maintain a uniformly moist condition within the mass. The worm tea that drips from the bottom of the raised bed is collected and re-misted over the bed with additional added water to maintain the requisite uniformly moist condition of the bed. Beginning after two weeks, a fraction of the worm tea that drips from the bottom of the bed is harvested for further processing into the final product. The process of feeding, misting, and harvesting continues for an additional ten weeks. The worm tea collected throughout the ten week period is collected, filtered, and is adjusted to a pH in the range of about 6.8 to 7.8. This pH adjustment preferably occurs by means of aeration wherein the filtered worm tea is aerated to achieve the proper pH. Finally, a surfactant is added to the pH adjusted preparation to aid absorption through the skin and improve the efficacy of the preparation.

DETAILED DESCRIPTION OF THE INVENTION

An elevated worm bed in the general form of a rectangular prism with a slatted bottom is elevated on a frame above a plastic catchment to collect worm tea produced during the process. About 7 parts by weight of shredded raw paper is evenly distributed along the bottom slats as an underlayment. The bed is populated with 10 parts by weight of each of three species of earthworms: *Eisenia fetida, Lumbricus rubellus,* and *Perionyx excavates*. The worms are fed weekly. The feeding regimen comprises: 1) A first layer of about 180 parts by weight of organic garbage comprising fruits, vegetables, and raw paper products; and, 2) A second layer of about 0.75 parts by weight of finely crushed volcanic grit comprising: a) About 9.9% by weight of Hawaiian black sand volcanic rock; b) About 9.9% by weight of Tennessee brown volcanic rock; c) About 9.9% by weight of Azomite® volcanic rock; d) About 59.6% by weight of zeolite volcanic rock; e) About 9.9% by weight of volcanic dolomite; and, f) About 0.8% by weight of Biozome® microbial soil enhancer. These weekly feeding layers are overseeded with about 40 parts by weight of washed dairy cow manure top dressing. The bed must be maintained at a temperature in the range of about 45° F. to about 75° F. The bed is misted daily with about 55 parts by weight to about 125 parts by weight of natural spring water. This achieves a consistently moist character in the bed. After each misting, a fraction of worm tea containing dissolved material derived from the worm casts deposited in the bed is collected in the plastic catchment. Each day, the fraction of worm tea collected the previous day is recycled by adding it to the misting water applied to the bed that day. After about two weeks, about 5 to about 8 parts by weight of the worm tea collected in the plastic catchment every day is harvested for conversion into final product. This process continues for ten weeks whereupon the worm tea collected throughout the ten week period is filtered to remove any large particulate matter and the resulting preparation is adjusted by means of aeration to a pH falling in the range of about 6.8 to about 7.8. As a final step, to each U.S. gallon of preparation produced, about 1 ml of Earth Juice® Assist is added. This preparation includes a surfactant that aids in absorption through the skin and improves the preparation's efficacy.

In an exemplary embodiment of the present invention, an elevated earthworm bed in the general form of a rectangular prism 8 ft. in length by 4 ft. in width by 1 ft. in depth with a slatted bottom is elevated on a frame above a plastic catchment for worm tea produced during the process. About 7 pounds of shredded raw paper is evenly distributed along the bottom slats as an underlayment. The bed is populated with about 10 pounds *Eisenia fetida* earthworms, 10 pounds *Lumbricus rubellus* earthworms, and 10 pounds of *Perionyx excavates* earthworms. According to this first exemplary embodiment of the present invention, the weekly feeding regimen comprises: 1) A first layer of about 180 pounds of organic garbage comprising fruits, vegetables, and raw paper products; and, 2) A second layer of about 12 ounces of finely crushed volcanic grit comprising: a) About 9.9% by weight of Hawaiian black sand volcanic rock; b) About 9.9% by weight of Tennessee brown volcanic rock; c) About 9.9% by weight of Azomite® volcanic rock; d) About 59.6% by weight of zeolite volcanic rock; e) About 9.9% by weight of volcanic dolomite; and, f) About 0.8% by weight of Biozome® microbial soil enhancer. These weekly feeding layers are overseeded with about 40 pounds of washed dairy cow manure top dressing.

The bed is maintained at a temperature in the range of about 45° F. to about 75° F. and misted daily with about 7 to about 15 U.S. gallons of water to achieve a uniformly moist consistency throughout the bed. After each misting, a fraction of worm tea containing dissolved material derived from the worm casts deposited in the bed is collected in the plastic catchment below the bed. Each day, the worm tea collected the previous day is recycled and added to the misting water applied to the bed that day. After about two weeks, about 0.6 to about 0.9 U.S. gallons of the worm tea collected in the plastic catchment every day is harvested for conversion into final product while the rest is recycled into the next day's misting water. This process continues for ten weeks. The amount of worm tea produced each week varies between about 4.0 and 6.0 U.S. gallons per week. The worm tea collected throughout the ten week period is filtered to remove any large particulate matter and the resulting preparation is adjusted by means of aeration to a pH falling in the range of about 6.8 to about 7.8. Finally, to each U.S. gallon of preparation about 1 ml of Earth Juice® Assist is added.

Those having skill in the art will recognize that the exemplary embodiment described above is just one of many, and that the apparatus used to create the preparation may be scaled up or down, as necessary, to increase or decrease production as desired.

The resulting preparation is roughly the viscosity of water and is used primarily as a spray mist topically applied as needed to relieve the itching and inflammation associated with psoriatic lesions and topical skin maladies such as non-specific skin rash, eczema, and acne. Ordinarily, in the early phases of treatment the sufferer will apply the preparation as needed. After a few weeks most sufferers will only apply the preparation twice a day.

It will be readily appreciated that misted liquid is not the sole means of application. Those having skill in the art will recognize that the preparation may be mechanically intermixed with any of a number of conventional ointments and creams such as petroleum jelly, beeswax, lanolin, Shea butter, and cocoa butter.

The effectiveness of the preparation in the treatment of itching and inflammation associated with psoriasis and other common skin maladies was tested by means of a single blind study administered by licensed medical practitioners over a period of three months. The following test cohost presented in the ordinary course for medical treatment for the following conditions:

TABLE 1

| Diagnosis | Cohort Size | Improvement % |
|---|---|---|
| Psoriasis | 10 | 100% |
| Non-specific Skin Rash* | 15 | 100% |
| Eczema | 10 | 70% |
| Acne | 6 | 83% |
| Fungal Infection | 4 | 100% |
| Rosacea | 3 | 100% |
| Sunburn | 2 | 100% |
| Insect Bite | 4 | 100% |
| Gangrenous Pyoderma | 1 | 100% |
| Keloids | 1 | 100% |
| Keratosis | 1 | 100% |

*The underlying cause of the rash was undiagnosed.

The test cohort was drawn from a general population of individuals seeking treatment for itching and inflammation secondary to a primary complaint. Members of the general population were offered their choice of conventional treatment or treatment using an experimental topical compound made by the method disclosed in the present application. The fraction of the general population that elected to undergo treatment using the experimental compound constituted the test cohort. Members of the test cohort were unaware of the nature of the compound or its manufacture; however, they were informed it was not a placebo.

The test application protocol consisted of applying a spray of the experimental compound once in the morning and once at night. For those members of the cohort suffering continual itching, they were instructed to apply the compound when needed. Acne was treated by soaking a compress and applying to afflicted areas once in the morning and once at night. Members of the test cohort were reevaluated by a physician after 48 and 72 hours. The physician recorded a positive or negative score indicating the amount of symptomatic improvement as observed by the physician and as reported by the patient.

The effectiveness of the preparation in the treatment of itching and inflammation associated with psoriasis and the other common skin maladies listed above (non-specific skin rash, eczema, and acne) was generally quite high (approximately 90% successful). The sample sizes for fungal infections, dermatitis, rosacea, sunburn, insect bite, gangrenous pyoderma, keloids, and keratosis were individually relatively small and statistically less significant. Nonetheless the data suggests that the preparation is at least somewhat effective in these cases.

What is claimed is:

1. A method of making a preparation for the treatment of itching and inflammation, said method comprising the steps of:
 a) providing an elevated, slatted worm bed with catchment to capture fluid dripping from the bottom of the worm bed;
 b) placing about 7 parts by weight of paper underlayment along the bottom layer of said worm bed;
 c) placing about 10 parts by weight of each of three species of earthworms on top of the underlayment:
  a. *Eisenia fetida;*
  b. *Lumbricus rubellus;*
  c. *Perionyx excavates;*
 d) immediately, and once weekly thereafter, feeding the worms wherein the feeding regimen comprises:
  a. a first layer of about 180 parts by weight of organic garbage comprising fruits, vegetables, and raw paper products;
  b. a second layer of about 0.75 parts by weight of finely crushed volcanic grit comprising:
   i. about 9.9% by weight of Hawaiian black sand volcanic rock;
   ii. about 9.9% by weight of Tennessee brown volcanic rock;
   iii. about 9.9% by weight of Azomite® volcanic rock;
   iv. about 59.6% by weight of zeolite volcanic rock;
   v. about 9.9% by weight of volcanic dolomite; and,
   vi. about 0.8% by weight of a microbial soil enhancer;
  c. a third layer of about 40 parts by weight of washed dairy cow manure;
 e) maintaining the bed at a temperature within the range of about 45° F. to about 75° F.;
 f) performing the following step each day for the first two weeks:
  a. misting the bed with about 55 parts by weight to about 125 parts by weight of natural spring water admixed with the fluid drippings collected in a plastic catchment from the previous day's misting, if any;
 g) performing the following steps each day after the first two weeks:
  a. harvesting about 5 to about 8 parts by weight of the fluid drippings collected in the plastic catchment from the previous day's misting for processing into finished product by means of steps i) through k), inclusive; and
  b. misting the bed with about 55 parts by weight to about 125 parts by weight of natural spring water admixed with the balance of the fluid drippings collected in the plastic catchment from the previous day's misting;
 h) performing steps d) through g) inclusive over a period of 12 weeks;
 i) filtering the fluid drippings harvested after the first two weeks to remove any large particulate matter;
 j) adjusting the pH of the fluid drippings harvested after the first two weeks to a pH in the range of about 6.8 to about 7.8;
 k) adding about 1 ml of a surfactant per U.S. gallon of the pH-adjusted fluid drippings to obtain said preparation.

* * * * *